United States Patent
Zatta

(10) Patent No.: US 11,534,207 B2
(45) Date of Patent: Dec. 27, 2022

(54) CORRECTIVE ANGLE PEDICLE SCREW TECHNOLOGY

(71) Applicant: Next Orthosurgical, Inc., Vista, CA (US)

(72) Inventor: Daniel Zatta, Vista, CA (US)

(73) Assignee: Next Orthosurgical, Inc., Vista, CA (US)

(*) Notice: Subject to any disclaimer, the term of this patent is extended or adjusted under 35 U.S.C. 154(b) by 450 days.

(21) Appl. No.: 16/373,483

(22) Filed: Apr. 2, 2019

(65) Prior Publication Data

US 2020/0253642 A1    Aug. 13, 2020

Related U.S. Application Data

(60) Provisional application No. 62/804,075, filed on Feb. 11, 2019.

(51) Int. Cl.
*A61B 17/70* (2006.01)

(52) U.S. Cl.
CPC ...... *A61B 17/7011* (2013.01); *A61B 17/7032* (2013.01); *A61B 17/7035* (2013.01)

(58) Field of Classification Search
CPC ............ A61B 17/7011; A61B 17/7032; A61B 17/7035; A61B 17/7034; A61B 17/7037; A61B 17/7038
See application file for complete search history.

(56) References Cited

U.S. PATENT DOCUMENTS

| | | | |
|---|---|---|---|
| 7,678,137 B2 * | 3/2010 | Butler | A61B 17/7034 606/246 |
| 9,131,962 B2 * | 9/2015 | Cahill | A61B 17/7037 |
| 2005/0080415 A1 * | 4/2005 | Keyer | A61B 17/7038 606/278 |
| 2006/0195098 A1 * | 8/2006 | Schumacher | A61B 17/7037 606/286 |
| 2009/0036935 A1 | 2/2009 | Jackson | |
| 2009/0163955 A1 | 6/2009 | Moumene et al. | |
| 2010/0249846 A1 | 9/2010 | Simonson | |
| 2013/0184759 A1 | 7/2013 | Rinehart et al. | |
| 2015/0282842 A1 | 10/2015 | Beyar et al. | |

FOREIGN PATENT DOCUMENTS

DE    102016215694 A1    2/2018

OTHER PUBLICATIONS

International Search Report and Written Opinion in PCT/US2020/014465, dated May 14, 2020.
International Preliminary Report on Patentability for Application No. PCT/US2020/014465, dated Aug. 26, 2021, 8 pages.

* cited by examiner

*Primary Examiner* — Ellen C Hammond

(57) ABSTRACT

A pedicle screw system applicable to affixation medical systems is provided. The system comprises a screw tulip comprising a rod receiving channel configured to receive a spinal rod, a shank configured to anchor the screw tulip and spinal to a pedicle. A bushing disposed between an interior surface of the screw tulip and a first end of the shank, wherein the first side of the bushing channel is defined by a top edge of a first wall of the bushing, a second side of the bushing channel is defined by a top edge of a second wall of the bushing, and the bushing channel is set at an angle defined by the top edge of the first wall and the top edge of the second wall.

13 Claims, 7 Drawing Sheets

CORRECTIVE ANGLE PEDICLE SCREW TECHNOLOGY

CROSS-REFERENCE TO RELATED APPLICATIONS

The present application claims the benefit of and priority to U.S. Provisional Patent Application No. 62/804,075, filed Feb. 11, 2019, which is hereby incorporated herein by reference in its entirety.

DESCRIPTION OF RELATED ART

There are various devices and systems for fixation of bone segments. One type of device is a pedicle screw. The pedicle screw provides a technique of gripping a spinal segment. A conventional pedicle screw includes a rod-receiving component to mount a rod. The rod-receiving component is often referred to as a "tulip."

A pedicle screw system may be polyaxial or monoaxial. A monoaxial pedicle screw system may have the tulip fixedly attached, or formed as part of, the screw itself. The monoaxial pedicle screw system does not permit rotation of the tulip relative the screw. A polyaxial screw system may be formed of multiple parts. Namely, the tulip and screw may be separate parts that attach together in a manner that allows the tulip to rotate relative to the screw.

BRIEF DESCRIPTION OF THE DRAWINGS

The present disclosure, in accordance with one or more various embodiments, is described in detail with reference to the following figures. The figures are provided for purposes of illustration only and merely depict typical or example embodiments.

The figures are not exhaustive and do not limit the present disclosure to the precise form disclosed.

DETAILED DESCRIPTION

For ease of discussion, the technology disclosed herein will be described with respect to the example pedicle screw system 100 illustrated in FIG. 1. The pedicle screw system 100 is presented for explanation only and is not intended to limit the scope of the subject matter of the present disclosure to any particular pedicle screw system. A person of ordinary skill in the art would understand the subject matter to be applicable to all pedicle screw systems.

Figure 1:
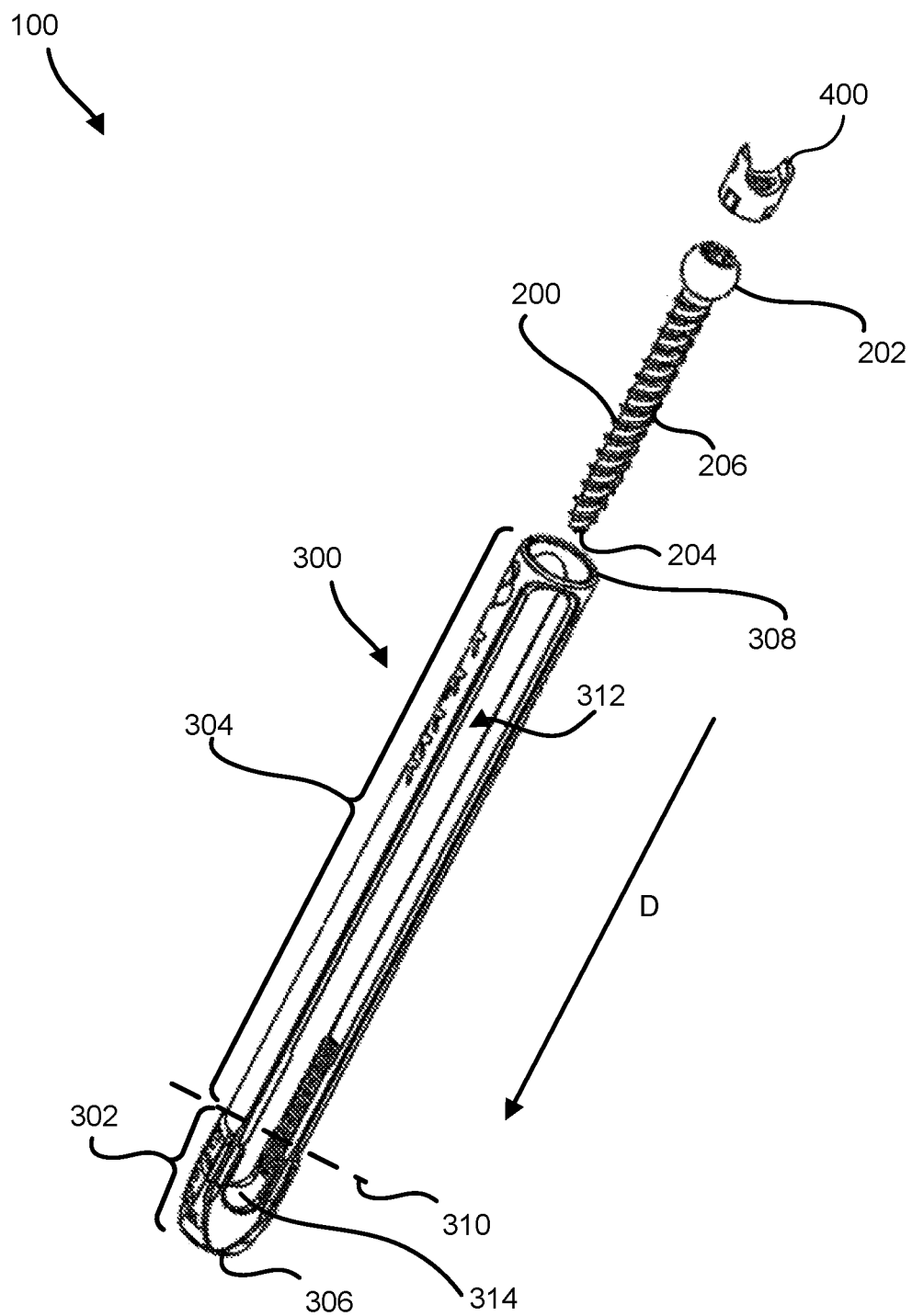
FIG. 1 illustrates an example pedicle screw system in accordance with embodiments of the technology disclosed herein.

Referring to FIG. 1, the pedicle screw system 100 may comprise one or more of a shank 200, a head component 300, a bushing 400, and/or other components. One or more of the components of the pedicle screw system 100 may be assembled through insertion of various components into other ones of the components along an assembly direction "D." The assembly direction D may be in-line with a direction of insertion of the screw body into a pedicle of a vertebrae of a subject (not shown). One or more components of the pedicle screw system 100 may be formed from one or more materials including, but not limited to, one or more of plastic, metal, and/or other materials. By way of non-limiting illustration, one or more components of the pedicle screw system 100 may be formed from titanium.

As stated, pedicle screw system 100 may include a shank 200. Shank 200, also referred to as a bone screw or screw, anchors the pedicle screw system 100 in the pedicle. Shank 200 may comprise one or more of a first end 202, a second end 204 opposite the first end 202, and one or more male threads including thread 206, and/or other components. In various embodiments, the shank 200 may include one or more flutes to provide a cutting edge for the shank 200. The one or more threads may define a major diameter of the shank 200. The second end 204 may comprise a tip of the shank 200 that may be inserted into a pedicle of a vertebrae of a subject. In various embodiments, the first end 202 may be configured to couple to a specific head component 300, while in other embodiments the first end 202 may be configured to couple to a plurality of different head components. The assembly direction D may comprise a direction extending from the first end 202 to the second end 204 of shank 200. In some implementations, the overall length of the screw body from first end 202 to second end 204 may be in the range of thirty to 150 millimeters, and/or other lengths.

In various embodiments, the shank 200 may be a single component as illustrated in FIG. 1, while in other embodiments the shank 200 may comprise one or more components configured to mate. As a non-limiting example, in some embodiments the first end 202 may be constructed as a separate component configured to mate with the screw body, comprising the second end 204 and the threads 206. The type of shank 200 implemented is a non-limiting factor with respect to the scope of the present disclosure. A person of ordinary skill in the art would understand that the embodiments of the technology disclosed herein are applicable to a multitude of different pedicle screw designs.

The head component 300 may be a pedicle screw tulip and/or other device. As illustrated in FIG. 1, the head component 300 may comprise a screw tulip 302 with an extension tower 304 extending from the screw tulip 302 to a distal end 308 of the head component 300 from the screw tulip 302. Extension towers 304 or extended screw heads are generally used in minimally invasive spinal surgery (MIS)

systems. In various embodiments, the extension tower 304 and the screw tulip 302 may be formed as a single component, and in some embodiments the extension tower 304 may be designed to break off from the screw tulip 302 after the pedicle screw system 100 is installed. In other embodiments, the extension tower 304 may comprise an extender or other reusable extension tool which may be connected to the screw tulip 302 to assist in guiding medical equipment during installation of the pedicle screw system 100 and subsequently removed when the surgery is complete. Although illustrated as having an extension tower 304, in various embodiments the screw tulip 302 may be used as a single component without the extension tower 304. The screw tulip 302 may also include a U-shaped rod receiving channel 314 in various embodiments. The rod receiving channel 314 may be used for coupling a rod (not shown) to the head component 300 during operative use in fixing bone segments together.

The screw tulip 302 may include an axial bore (not shown) comprising a passage extending from an opening at a first end 306 of the screw tulip 302 to an opening 310 of the screw tulip 302. The axial bore may be aligned with a longitudinal axis of the head component 300. The axial bore may define the interior surface of the screw tulip 302, in various embodiments the interior surface may define a bore diameter of the axial bore of the screw tulip 302. A channel 312 in the interior of the extension tower 304 may extend from the opening 310 to the distal end 308, providing a path through which medical equipment may be inserted and/or manipulated. In various embodiments, the channel 312 may have the same dimensions as the axial bore of the screw tulip 302, while in other embodiments the channel 312 may have larger dimensions than the axial bore of the screw tulip 302. When the pedicle screw system 100 is assembled, the first end 202 of the shank 200 may seat against the interior surface of the screw tulip 302.

The bushing 400 may be configured to be inserted into the axial bore of the screw tulip 302 along the insertion direction D from the distal end 308 of the head component 300. In embodiments without the extension tower 304, the bushing 400 may be configured to be inserted into the axial bore of the screw tulip 302 along the insertion direction D from the opening 310 of the screw tulip 302. The insertion of the bushing 400 in the assembled mode of the pedicle screw system 100 may cause the bushing 400 to frictionally engage between the interior surface of the screw tulip 302 and the first end 202 of the shank 200 to maintain the seat of the first end 202 against the interior surface of the screw tulip 302.

In various embodiments, the pedicle screw system 100 may be configured such that the first end 202 of the shank 200 is prevented from passing through the axial bore of the screw tulip 302 of the head component 300. That is, in various embodiments, the major diameter of the shank 200 may be larger than the narrowest part of the bore diameter of the axial bore of the screw tulip 302.

Pedicle screw systems are generally used in surgical procedures concerning the spine, enabling a spinal rod to be affixed to the spine to fuse one or more spinal segments together. Due to the shape of the spine, spinal rods generally have some angle of curvature. Where a short segment of the spine is being fused, or in MIS systems with extension towers, this curvature can cause undesired results with current pedicle screw system design. The screw tulip used in current pedicle screw systems is configured to normalize with the spinal rod after installation, resulting in the tulip resting perpendicular to the surface of the rod at the surgical location. In such cases, the tulips may arch towards each other, resulting in pinching of the patient's skin and increasing the chance of the patient developing localized necrosis. Moreover, in MIS systems or when tulips with extension towers are utilized, the curvature could result in the towers interfering with each other. During surgery, such interference can result in tissue pinching (similar to the short segment situation). Moreover, such interference requires the surgeon to constantly adjust the towers (e.g., pull them apart), which can result in more stress onto the surrounding tissues and other parts of the patient's anatomy.

Embodiments of the technology disclosed herein accounts for the curvature of the spinal rod to reduce the impact of the screw tulip in such situations. By offsetting the trajectory of the tulip, embodiments discussed herein can keep the tulips from arcing towards each other. If a spinal rod having a large curvature is being affixed, a first tulip could be offset to a first degree in one direction and a second tulip could be offset to a second degree, thereby introducing a combined degree of bias into the system to avoid interaction of the tulips.

Figure 2A:
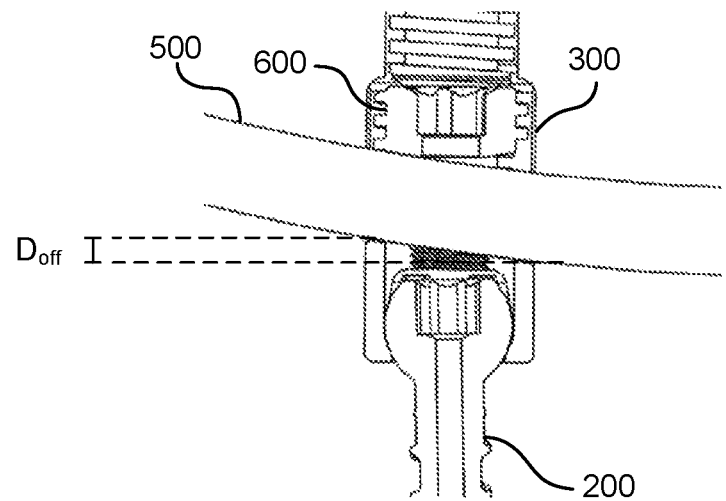
FIG. 2A is a cross-sectional view of an example interface between various components of a pedicle screw system and a spinal rod in accordance with embodiments of the technology disclosed herein.
Figure 2B:
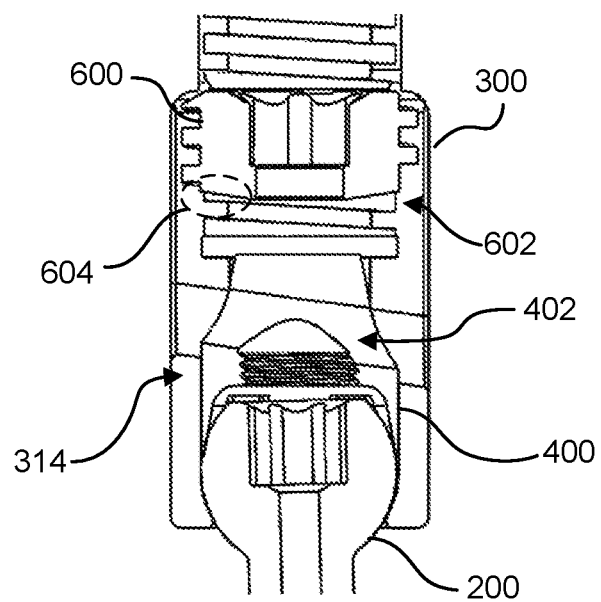
FIG. 2B is a cross-sectional view of an example pedicle screw system in accordance with embodiments of the technology disclosed herein.

FIGS. 2A and 2B are cross-sectional views illustrating the interface between a spinal rod 500, the head component 300, the bushing 400, the shank 200 and the set screw 600 in accordance with embodiments of the technology of the present disclosure. Where elements in the figures are identified using like reference characters, the discussion associate with like referenced elements should be interpreted as applying to the same element in each figure.

Referring to FIG. 2A, the pedicle screw system illustrates the spinal rod 500 interfaced with the head component 300 and the shank 200. Although not explicitly shown, a bushing 400 is installed within the head component 300 and coupled to the shank 200 (as shown in FIG. 2B). As shown in FIG. 2A, the spinal rod 500 is not straight but has a curvature. The curvature of the spinal rod 500 is dependent on the location on the spine to which the pedicle screw system is installed. In various embodiments, the curvature of the spinal tab 500 may be consistent across the length of the spinal rod 500. In other embodiments, the spinal rod 500 may have a first curvature angle on a first portion of the rod, a second curvature angle on a second portion of the rod, and so on for the length of the spinal rod 500. One or more of the portions of the spinal rod 500 may have the same curvature as one or more different portions of the spinal rod 500 in some embodiments, while in other embodiments one or more portions of the spinal rod 500 may be straight (i.e., zero curvature angle).

The bushing 400 and set screw 600 may be configured to add an offset $D_{off}$ (shown in FIG. 3A) to the rod receiving channel 314 of the head component 300 to account for the curvature of the spinal rod 500. As shown in FIG. 2B, the rod receiving channel 314 of the head component 300 comprises a shaft through the head component 300. In some embodiments, the rod receiving channel 314 may be straight across the width of the screw tulip 302 or may be slanted across the width of the screw tulip 302. In other embodiments, the rod receiving channel 314 may be stepped. As used in the present disclosure, a channel is "stepped" where the bottom of the rod receiving channel 314 at a first side of the screw tulip 302 is higher than the bottom of the rod receiving channel 314 at the opposite side of the screw tulip 302 to form the shape of a step of a staircase, with the bottom of the rod receiving channel 314 extending straight across from the opposite side of the screw tulip 302 to the wall of the screw tulip 302 comprising the bottom of the rod receiving channel 314 at the first side of the screw tulip 302. The size of the rod receiving channel 314 may vary in various embodiments based on the design of the spinal rod 500 used in a particular implementation. Comparing the rod receiving channel 314 of FIG. 2B with the spinal rod 500 of FIG. 2A shows that the rod receiving channel 314 follows the curvature of the spinal rod 500.

Regardless of the particular design, the rod receiving channel 314 must be proportioned such that it creates sufficient space for the spinal rod 314 to effectively interact with the shank 200, bushing 400, and set screw 600 to secure the pedicle screw system to the pedicle. Sufficient space means that the circumference of the rod receiving channel 314 is larger than the circumference of the bushing channel 402. In various embodiments, sufficient space may require the rod receiving channel 314 to be dimensioned such that it extends below the bushing channel 402 (shown in FIG. 2B). Having the rod receiving channel 314 extend below the bushing channel 402 allows for the spinal rod 500 to be compressed against the shank 200 and the bushing 400 through application of pressure from the set screw 600. In other embodiments the rod receiving channel 314 may extend below and above the bushing channel 402. In still other embodiments, the rod receiving channel 314 may comprise a groove resting below the bushing channel 402, while in other embodiments the rod receiving channel 314 may comprise a bore hole through the head component 300. The rod receiving channel 314 may have a circular, elliptical, or other geometric shape. In various embodiments, the rod receiving channel 314 may be dimensioned similar to current rod receiving channels.

Figure 3A:
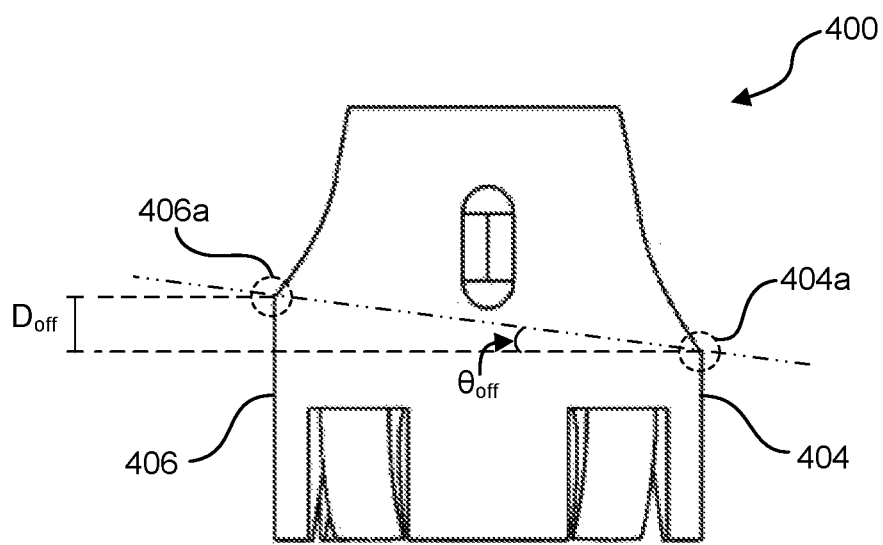
FIG. 3A shows a side view of the bushing illustrated in FIG. 2B in accordance with embodiments of the technology disclosed herein.

FIG. 3A shows a side view of the bushing 400 illustrated in FIG. 2B. As illustrated in FIG. 3A, to provide the offset $D_{off}$, the bushing 500 may be manufactured in various embodiments such that a bushing channel 502 is set at an offset angle $\theta_{off}$. The offset angle $\theta_{off}$ is defined based on the positions of a top edge 404a of a first wall 404 of the bushing 400 and a top edge 406a of a second wall 406 of the bushing 400. As can be seen in FIG. 3A, the offset angle $\theta_{off}$ results in the top edge 404a being lower than the top edge 406a, resulting in the bushing channel 402 of the bushing 400 being set at the desired offset $D_{off}$. In various embodiments, the offset angle $\theta_{off}$ may be between 1° and 20°, inclusive. In some embodiments, the offset angle $\theta_{off}$ may be 5°, 7.5°, and 10.

Figure 3B:
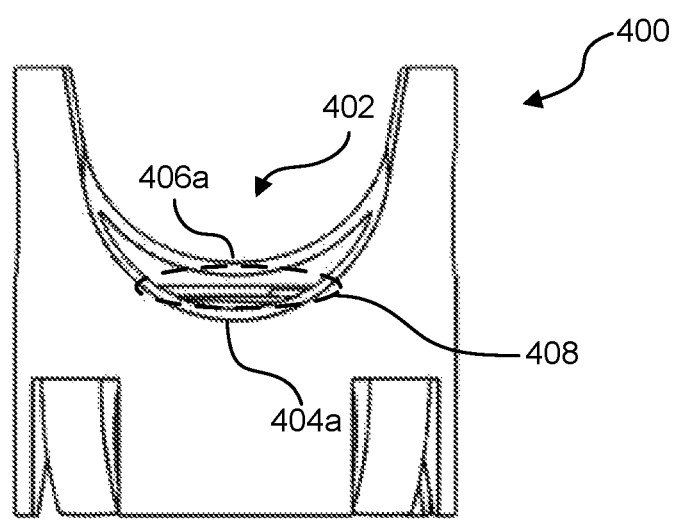
FIG. 3B shows a frontal view of the bushing illustrated in FIG. 2B in accordance with embodiments of the technology disclosed herein.

FIG. 3B shows a frontal view through the bushing channel 402 of the bushing 400, illustrating the difference in height between the top edge 404a of the first wall 404 and the top edge 406a of the second wall 406. As can be seen, an interior surface 408 of the bushing 400 is visible when looking through the bushing channel 402 from the top edge 404a to the top edge 406a. When the bushing 400 is combined with the head component 300, the bushing channel 402 enables the screw tulip 302 of the head component 300 to not rest perpendicular to the spinal rod 500, reducing the possibility of undesirable skin pinching and/or extension tower interaction. In various embodiments, the bushing channel 402 may be flat, stepped, or curved across from top edge 404a to top edge 406a.

Referring back to FIG. 2A, the spinal rod 500 is held in place within the pedicle screw system by a set screw 600 in many embodiments. The set screw 600 may be made of any material suitable for use in medical devices, including any material discussed above with respect to FIG. 1. To account for the offset $D_{off}$ due to the bushing channel 402, the set screw 600 may be constructed in some embodiments such that an end 602 of the set screw 600 contacts more surface area of the spinal rod 500.

As shown in FIG. 2B, an angled cut 604 may be made into the end 602 of the set screw 600. In various embodiments, the angled cut 604 may be configured to mirror the offset $D_{off}$ of the bushing channel 402, while in other embodiments the angled cut 604 may be less than or greater than the offset $D_{off}$. Because of the angled cut 604, as the set screw 600 is screwed down to secure the spinal rod 500 a larger amount of the end 602 will interface with the surface of the spinal rod 500, as opposed to just a small edge of the end 602 if no angled cut 604 is included, thereby providing greater stability and downward pressure on the spinal rod 500. In various embodiments, the angled cut 604 may be created through a conical cut of the end 602 of the set screw 600.

In some embodiments, the angled cut 604 may have a radius, increasing the surface contact with the spinal rod 500 even more. For example, the radius of the angled cut 604 may be manufactured to include a curvature corresponding to the lordosis or curvature of the spinal rod 500 in the portion of the spinal rod 500 passing through the head component 300. In some embodiments, the radius of the angled cut 604 may be less than or greater than the lordosis of the spinal rod 500.

In some embodiments, the set screw 600 may comprise an adjustable contact plate on the end 602 instead of an angled cut 604. An joint, such as a ball-and-socket joint, can be included to enable the adjustable contact plate to change its trajectory compared to the set screw 600 upon contacting the surface of the spinal rod 500. In this way, the surface area of the spinal rod 500 with which the set screw 600 contacts may be increased without the need to create the angled cut 604 in the end 602. to increase the surface area of the spinal rod 500 with which the set screw 600 may engage. In various embodiments, the socket may be located on the end 602 or the adjustable contact plate, with the ball joint located on the respective other component, while in other embodiments the placement of the elements of the joint mechanism can be reversed. The adjustable contact plate may be shaped in various embodiments in a similar manner as the angled cut 604 discussed above. For example, the adjustable contact plate may be shaped such that the adjustable contact plate is angled in accordance with a lordosis of the spinal rod 500 as discussed above with respect to the angled cut 604.

Figure 4B:
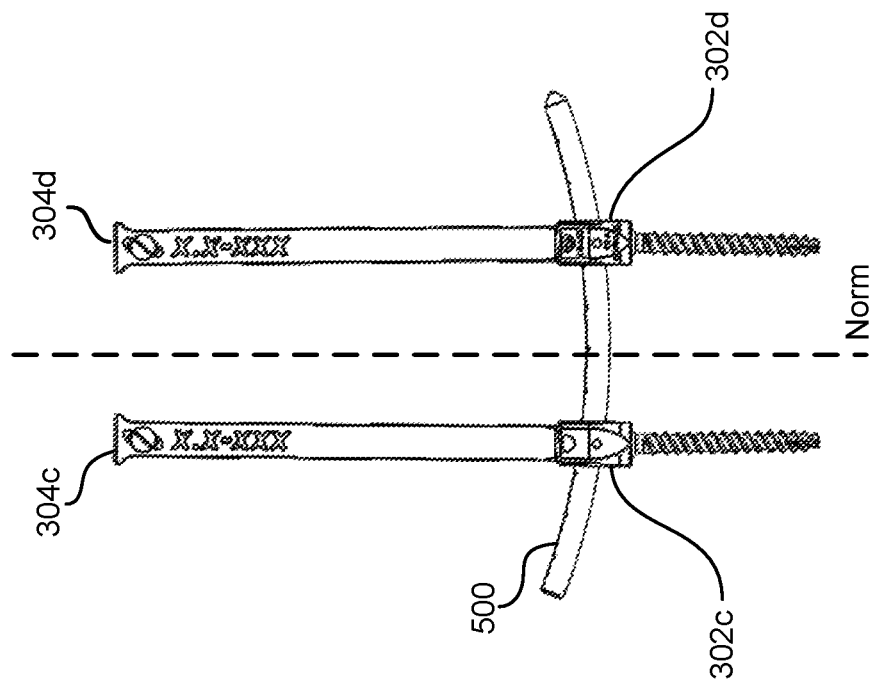
FIG. 4B illustrates an example pedicle screw system during installation in accordance with embodiments of the technology disclosed herein.
Figure 4A:
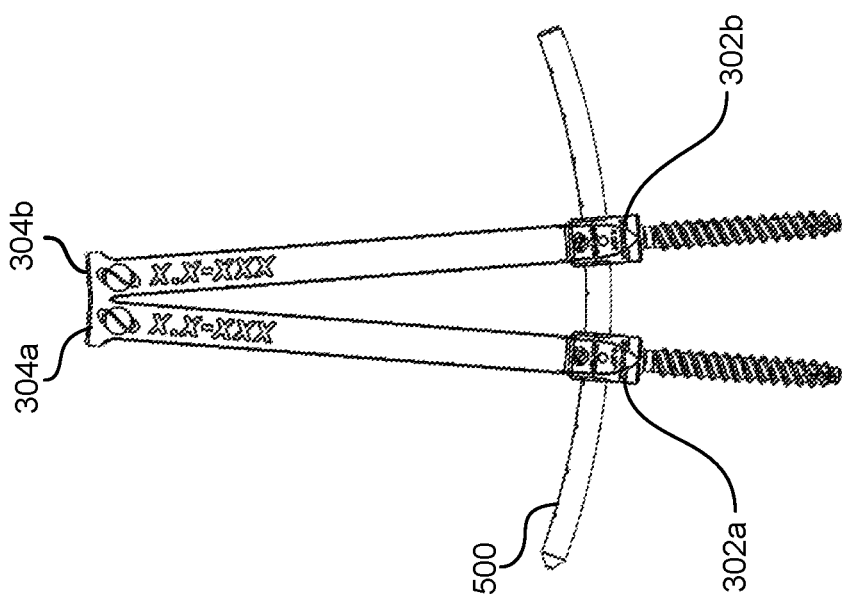
FIG. 4A illustrates a prior art pedicle screw system during installation.

FIGS. 4A and 4B provides a side-by-side comparison of traditional pedicle screw systems with extension towers and a pedicle screw system with extension towers in accordance with embodiments disclosed herein. FIG. 4A shows a current pedicle screw system with screw tulips 302a, 302b and extension towers 304a, 304b. As illustrated, the tulips 302a, 302b rest perpendicular to the surface of the spinal rod 500, resulting in the extension towers 304a, 304b being angled towards each other. This results in the towers 304a, 304b interfering with each other as shown in FIG. 4A. This interference would require the surgeon to physically separate and readjust the extension towers 304a, 304b constantly during surgery, increasing the strain on the patient's spine, tissue, and body and, thereby, increasing the risk of undesirable complications.

Figure 4C:
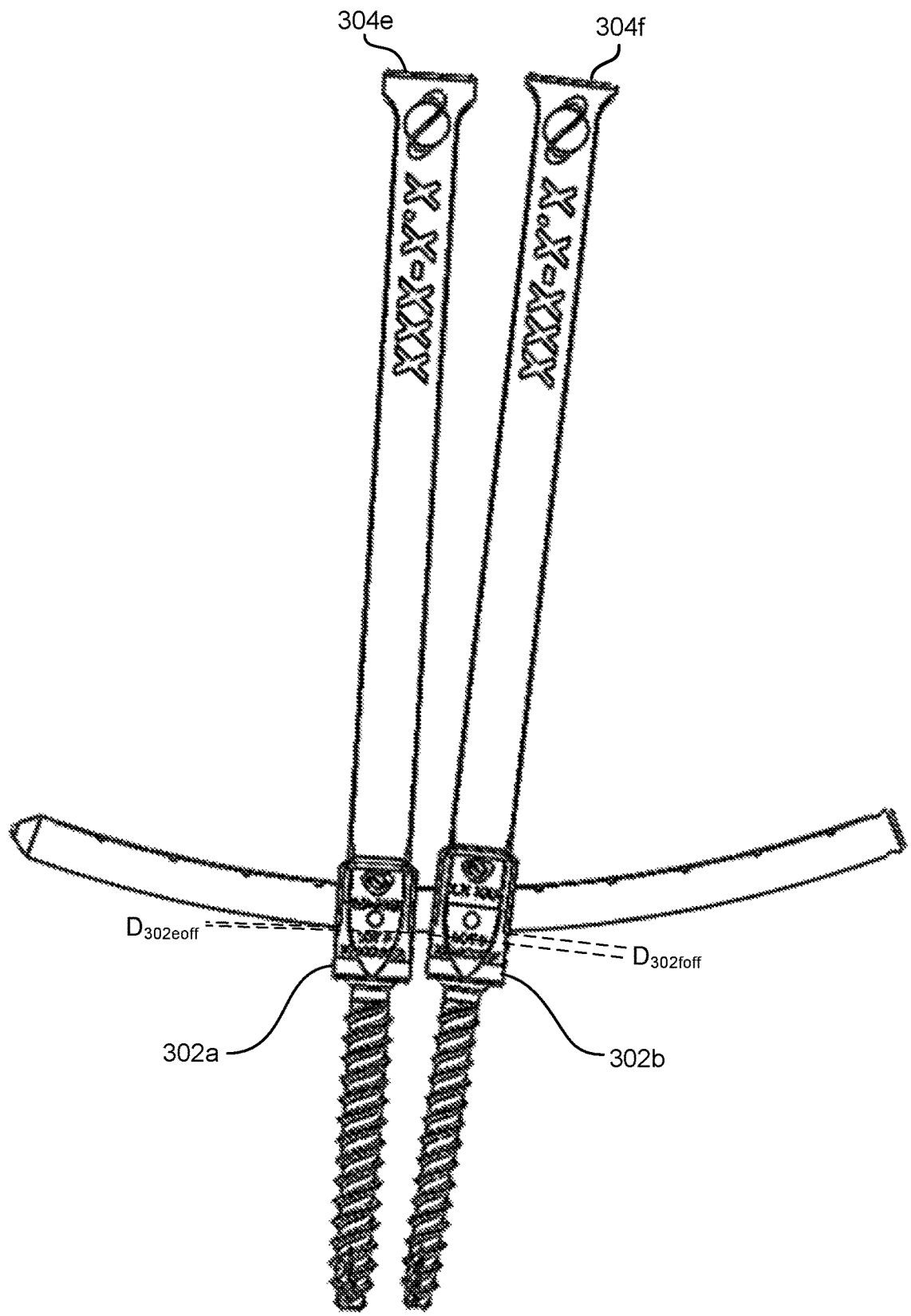
FIG. 4C illustrates another example pedicle screw system during installation in accordance with embodiments of the technology disclosed herein.

However, as illustrated in FIG. 4B, a pedicle screw system in accordance with embodiments of the present disclosure avoids such interaction. As shown, the screw tulips 302c, 302d are not perpendicular to the surface of the spinal rod 500, but instead offset. This results in the extension towers 304c, 304d not interfering with each. With such an arrangement, a surgeon can freely install the pedicle screw system without the need to constantly adjust the extension towers 304c, 304d, or the screw tulips 302c, 302d pinching the tissue between them and increasing the chance of necrosis. Moreover, as illustrated in FIG. 4B, by switching the direction of the bushing 400, the angle of screw tulips 302c, 302d may be the same, but in different directions. Moreover, as discussed above, the offset angle $\theta_{off}$ of the bushing 400 of each screw tulip can be different. FIG. 4C illustrates such an example pedicle screw system in accordance with embodiments of the technology disclosed herein. As shown, the screw tulip 302e is set at a first offset angle, and screw tulip 302f is set at a second offset angle. Due to the difference between the first offset angle and the second offset angle, the extension tower 304f is tilted at a greater angle $\theta_{304f}$ that the extension tower 304e (angle $\theta_{304e}$), resulting in different offsets $D_{302eoff}$, $D_{302foff}$ for each screw tulip 302e, 302f.

Figure 5:
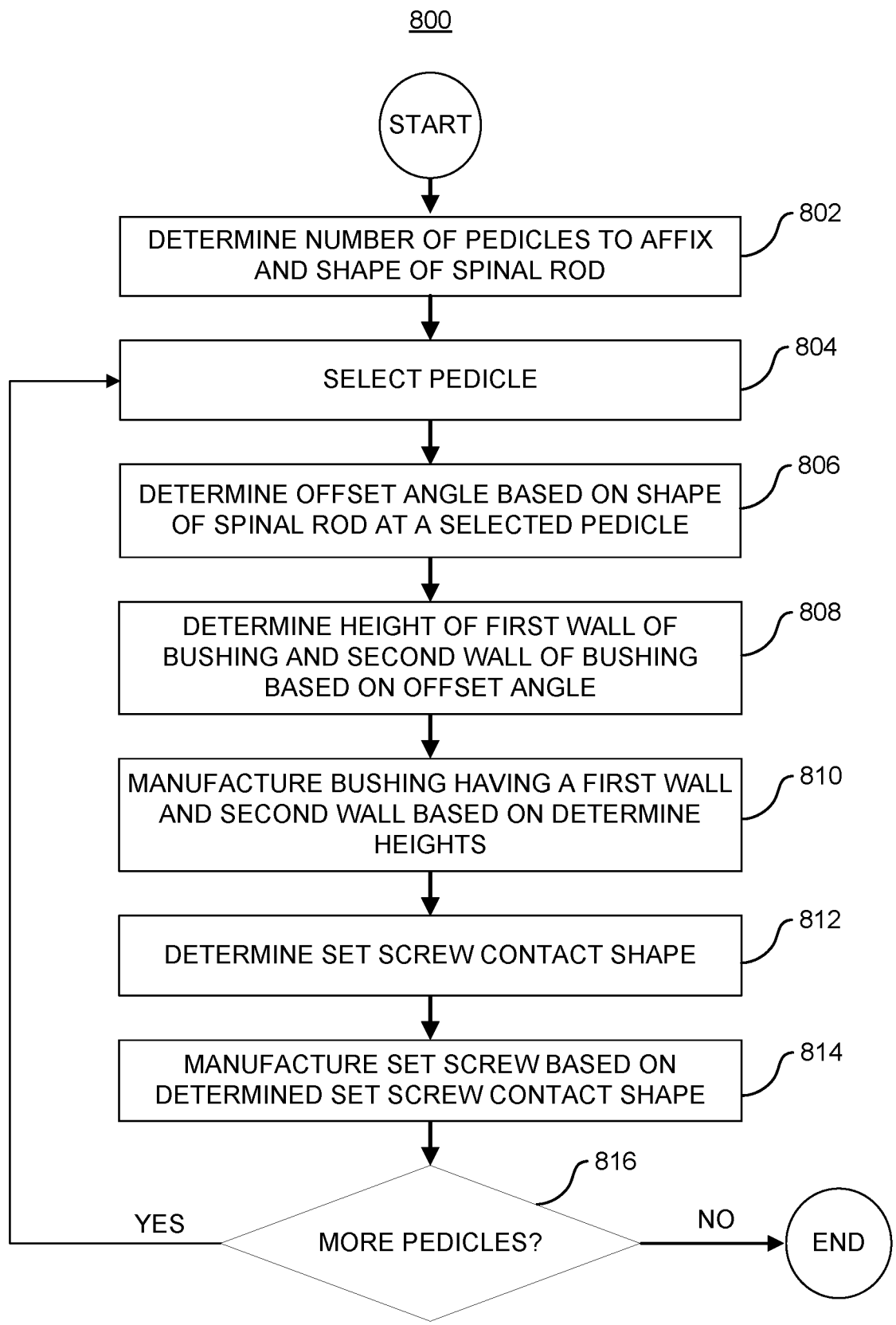
FIG. 5 is a method of manufacturing an example pedicle screw system in accordance with embodiments of the technology disclosed herein.

FIG. 5 illustrates an example method 800 of manufacturing a pedicle screw system in accordance with embodiments of the present disclosure. At operation 802, the number of pedicles to be affixed and the shape of the spinal rod is determined. In various embodiments, the number of pedicles and the shape of the spinal rod may be provided by a medical professional who is performing or associated with the intended surgical procedure. In other embodiments, the number of pedicles and the shape of the spinal rod may be determined based on measurement data of the intended area of the surgery. The shape of the spinal rod may vary across its length, similar to the spinal rod portions discussed above with respect to FIG. 2A.

At operation 804 a first pedicle is chosen. With respect to the selected pedicle, an offset angle is determined based on the shape of the spinal rod at operation 806. The offset angle may be determined in a similar manner as discussed above with respect to FIGS. 2A, 2B, 3A, and 3B.

At operation 808, a height of a first wall of the bushing and a second wall of the bushing is determined based on the determined offset angle. In various embodiments, determining the offset angle comprises determining a desired trajectory for a screw tulip such that the screw tulip would not rest perpendicular to the surface of the spinal rod, but instead sit on an angle compared to the spinal rod. As discuss with respect to FIGS. 2B, 3A, and 3B, the first wall and the second wall of the bushing may be manufactured such that the first wall has a larger height than the second wall, or the second wall has a larger height than the first wall. In this way, the bushing will have a bushing channel that is pitched according to the offset angle and will, when coupled to the screw tulip, result in the screw tulip being pitched at the desired trajectory. At operation 810 the bushing is manufactured having the first wall and the second wall at the determined heights, respectively.

At operation 812, the shape of the set screw is determined. In some embodiments, the determined shape may be such that the end of the set screw is similar to a standard set screw, with an end that is substantially straight across the width of the set screw. In other embodiments, the determined shape of the set screw may be an end with an angled cut, such as the angled cut 604 discussed above with respect to FIG. 2B. In still other embodiments, the determined shape of the set screw may include an end shaped according to a lordosis of the spinal rod. The shape of the set screw may be determined in various embodiments such that 50% or more of the set screw contacts the surface of the spinal rod when installed, while in other embodiments the set screw shape may be determined such that a greater amount of the surface area of the end of the set screw contacts the surface of the spinal rod compared to a standard set screw. The set screw may further comprise an adjustable contact plate, such as the adjustable contact plate discussed with respect to FIG. 2B, in some embodiments. At operation 814, the set screw is manufactured according to the determined set screw shape.

After the bushing and the set screw are manufactured, at decision 816 it is determined whether there are more pedicles in which a pedicle screw is to be anchored. A minimum of two pedicles are generally used in spinal fusion operations such as those discussed herein. If "YES," the method 800 goes back to operation 804 and the next pedicle is selected. The method 800 will continue to iterate through operations 804-816 as long as there is another pedicle in which a pedicle screw will be anchored. After bushings and set screws for all the pedicles are manufactured (i.e., the "NO" branch at 816), method 800 ends. Although the manufacture of the screw tulips and screws are not included in method 800 this should not be interpreted as limiting method 800 only to create pairs of bushings and set screws independent of the other components of the example pedicle screw system 100 discussed with respect to FIGS. 1, 2A, 2B, 3A, 3B, 4A, and 4B. Although not explicitly discussed, a person of ordinary skill in the art would understand that the bushing and set screw pairs created in accordance with method 800 can be manufactured as a set with a screw tulip and/or screw.

Figure 6:
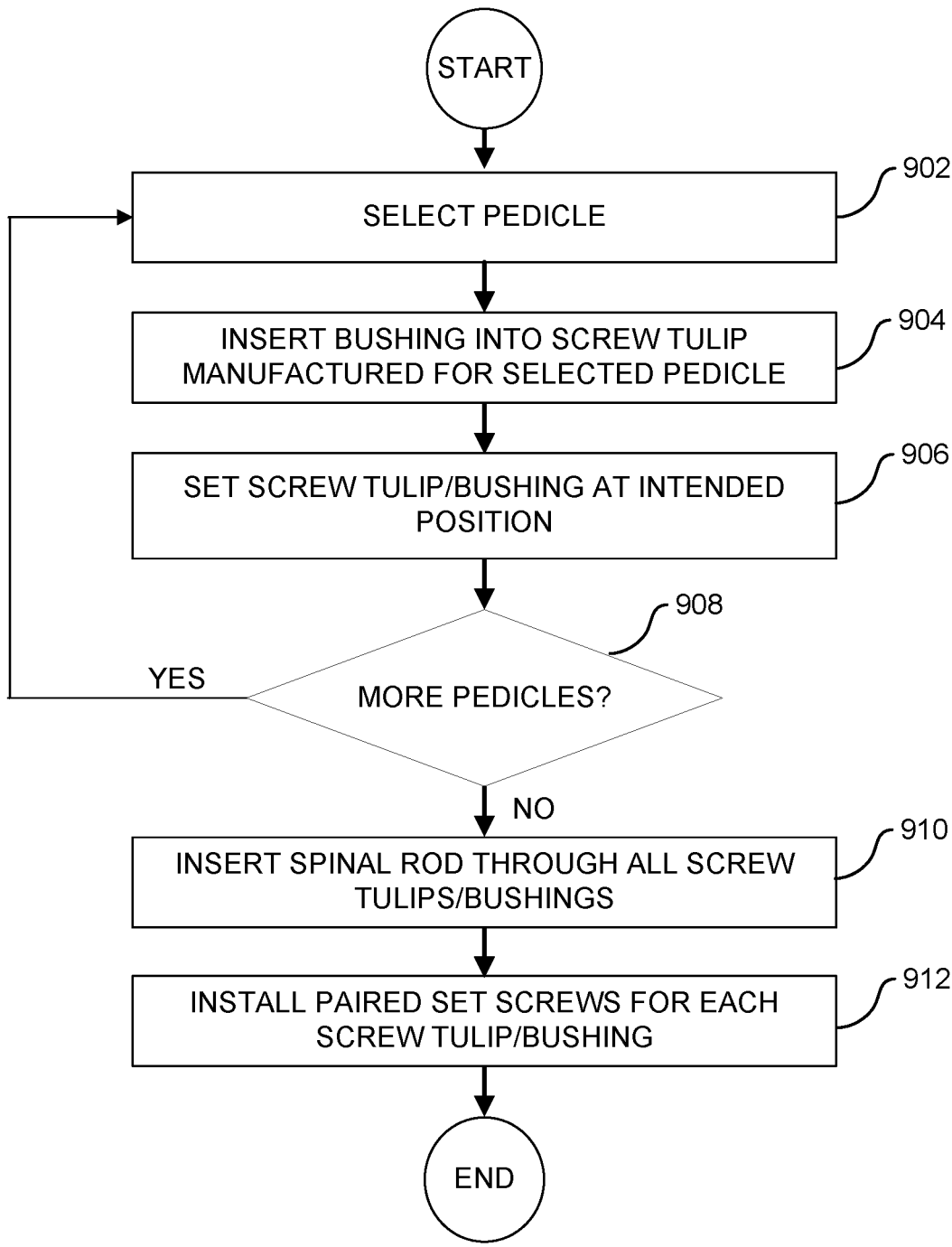
FIG. 6 illustrates an example method of installing a pedicle screw system in accordance with embodiments of the technology disclosed herein.

FIG. 6 illustrates an example method 900 of installing a pedicle screw system in accordance with embodiments of the technology of the present disclosure. Method 900 shall be described under the assumption that the required components of the pedicle screw system, such as the components discussed with respect to FIGS. 1, 2A, 2B, 3A, 3B, 4A, and 4B, have been manufactured. At operation 902, a pedicle is selected at which to begin installation. At operation 904, the bushing associated with the selected pedicle is inserted into the corresponding screw tulip, and at operation 906 the screw tulip/bushing pair is set at the intended position on the pedicle. The intended position may comprise a location on the surface of the pedicle and/or an designed orientation of the screw tulip/bushing pair. In various embodiments, the designed orientation may be an orientation whereby the rod-receiving channel of the screw tulip/bushing channel of the bushing are aligned in the direction of installation of the spinal rod. The orientation may also include the orientation of the manufactured bushing such that the first wall and the second wall are positioned to match the determined offset angle for the portion of the spinal rod at the selected pedicle. In various embodiments, the bushing may be inserted into the screw tulip prior to the screw tulip/bushing pair being set on the pedicle. In other embodiments, the bushing may be inserted into the screw tulip after the screw tulips has been set at the intended position on the pedicle. In various embodiments, setting the screw tulip/bushing at the intended position includes inserting the screw through the screw tulip/bushing in a manner similar to the manner of installation discussed with respect to FIG. 1.

If it is determined that there are more pedicles for which a pedicle screw has been designed at decision 908 (i.e., the "YES" branch), the method 900 returns to operation 902. Method 900 continues to iterate through operations 904-906 until all of the pedicles involved in the surgical procedure have been addressed (i.e., the "NO" branch).

Once all of the screw tulip/bushing pairs have been set, the spinal rod may be inserted through all of the screw tulips/bushings at operation 910. As discussed above with respect to FIGS. 1, 2A, 2B, 3A, 3B, 4A, and 4B, the spinal rod is inserted into the rod receiving channel of the screw tulip and the bushing channel of the bushing. In various embodiments, where the spinal rod has a curvature, the bushing channel of the respective bushing will assist in offsetting the screw tulip from the spinal rod such that the screw tulip will not reset perpendicular to the spinal rod after installation. Once the spinal rod is in place, the set screw paired with each respective screw tulip/bushing is installed at operation 912. In various embodiments, the set screw may be similar to the set screw 600 discussed above with respect to FIG. 2B. In some embodiments, each set screw may not be fully engaged against the spinal rod until it is determined that the spinal rod is correctly installed.

In some embodiments, operations 910 and 912 may occur in conjunction with operation 906 for each screw tulip/bushing individually where the spinal rod shape makes it difficult to thread the spinal rod through all of the screw tulips/bushings. In such embodiments, decision 908 would occur following operation 912.

Although the technology disclosed herein has been discussed with respect to a pedicle screw system, a person of ordinary skill in the art would understand that the technology is applicable to other screw or other affixation medical device systems (e.g., cervical, thoracic, lumbar, iliac, etc.). Moreover, a person of ordinary skill in the art would know that embodiments of the present disclosure are applicable to secure spinal connectors (e.g., lateral offset connectors) that are commonly used in pedicle screw systems to accommodate for a patient's anatomy.

In common usage, the term "or" should always be construed in the inclusive sense unless the exclusive sense is specifically indicated or logically necessary. The exclusive sense of "or" is specifically indicated when, for example, the term "or" is paired with the term "either," as in "either A or B." As another example, the exclusive sense may also be specifically indicated by appending "exclusive" or "but not both" after the list of items, as in "A or B, exclusively" and "A and B, but not both." Moreover, the description of resources, operations, or structures in the singular shall not be read to exclude the plural. Conditional language, such as, among others, "can," "could," "might," or "may," unless specifically stated otherwise, or otherwise understood within the context as used, is generally intended to convey that certain embodiments include, while other embodiments do not include, certain features, elements and/or steps.

Terms and phrases used in this document, and variations thereof, unless otherwise expressly stated, should be construed as open ended as opposed to limiting. Adjectives such as "conventional," "traditional," "normal," "standard," "known," and terms of similar meaning should not be construed as limiting the item described to a given time period or to an item available as of a given time, but instead should be read to encompass conventional, traditional, normal, or standard technologies that may be available or known now or at any time in the future. The presence of broadening words and phrases such as "one or more," "at least," "but not limited to" or other like phrases in some instances shall not be read to mean that the narrower case is intended or required in instances where such broadening phrases may be absent.

What is claimed is:

1. A pedicle screw system, comprising:
   a spinal rod having a curvature with a first curvature angle on a first portion of the rod and a second curvature angle on a second portion of the rod;
   multiple screw tulips, each individual screw tulip having a rod receiving channel configured to receive the spinal rod;
   individual shanks configured to anchor each individual screw tulip and spinal rod to a pedicle;
   individual bushings disposed within each individual screw tulip between an interior surface of each individual screw tulip and a first end of the individual shanks, the individual bushings comprising a bushing channel configured to receive the spinal rod; and
   multiple set screws configured to apply pressure to the spinal rod to compress the spinal rod against the first end of the individual shanks and the bushing;
   wherein a first side of the bushing channel is defined by a top edge of a first wall of a first bushing, a second side of the bushing channel is defined by a top edge of a second wall of the first bushing, and the bushing channel being set at a first angle defined by the top edge of the first wall and the top edge of the second wall;
   wherein a first side of a second bushing channel is defined by a top edge of a first wall of a second bushing, a second side of the second bushing channel is defined by a top edge of a second wall of the second bushing, and the second bushing channel being set at a second angle defined by the top edge of the first wall and the top edge of the second wall of the second bushing,
   wherein the first angle and the second angle are different; and
   wherein each individual screw tulip of the multiple screw tulips is configurable to align in independent directions.

2. The pedicle screw system of claim 1, the bushing channel comprising a flat bushing channel from the top edge of the first wall to the top edge of the second wall.

3. The pedicle screw system of claim 1, the bushing channel comprising a curved bushing channel from the top edge of the first wall to the top edge of the second wall.

4. The pedicle screw system of claim 3, wherein the curved bushing channel comprises a curve corresponding to the curvature of the spinal rod.

5. The pedicle screw system of claim 1, wherein the bushing channel comprises a stepped bushing channel from the top edge of the first wall to the top edge of the second wall.

6. The pedicle screw system of claim 1, wherein the rod receiving channel of a first screw tulip has a first circumference, the bushing channel has a second circumference, and the first circumference is larger than the second circumference.

7. The pedicle screw system of claim 6, wherein the rod receiving channel of the first screw tulip is set at an angle corresponding to the first angle of the bushing channel.

8. The pedicle screw system of claim 6, wherein the rod receiving channel of the first screw tulip is flat.

9. The pedicle screw system of claim 6, wherein the rod receiving channel of the first screw tulip is stepped.

10. The pedicle screw system of claim 1, wherein a first set screw comprises an angled cut at a first end of the first set screw configured to contact the spinal rod, the angled cut being conical.

11. The pedicle screw system of claim 10, wherein the angled cut has a radius corresponding to the curvature of the spinal rod.

12. The pedicle screw system of claim 1, wherein a first set screw comprises an adjustable contact plate affixed to a first end of the set screw configured to contact the spinal rod.

13. The pedicle screw system of claim 12, wherein the adjustable contact place has a curvature corresponding to the curvature of the spinal rod.

* * * * *